United States Patent
Dam

(10) Patent No.: US 9,226,985 B2
(45) Date of Patent: Jan. 5, 2016

(54) SANITIZING REMOTE CONTROLS AND HANDHELD DEVICES

(71) Applicant: Tuan Quoc Dam, Round Rock, TX (US)

(72) Inventor: Tuan Quoc Dam, Round Rock, TX (US)

(*) Notice: Subject to any disclaimer, the term of this patent is extended or adjusted under 35 U.S.C. 154(b) by 0 days.

(21) Appl. No.: 14/298,897

(22) Filed: Jun. 7, 2014

(65) Prior Publication Data

US 2014/0363335 A1 Dec. 11, 2014

Related U.S. Application Data

(60) Provisional application No. 61/832,794, filed on Jun. 8, 2013.

(51) Int. Cl.
*A61L 2/10* (2006.01)
(52) U.S. Cl.
CPC .......................................... *A61L 2/10* (2013.01)

(58) Field of Classification Search
CPC .......................................................... A61L 2/10
USPC ....................................... 250/455.11; 422/24
See application file for complete search history.

(56) References Cited

U.S. PATENT DOCUMENTS

| | | | |
|---|---|---|---|
| 5,185,532 A * | 2/1993 | Zabsky et al. ............ | 250/455.11 |
| 2010/0044582 A1 * | 2/2010 | Cooper et al. ........... | 250/455.11 |
| 2010/0127660 A1 * | 5/2010 | Cook et al. .................... | 320/108 |

* cited by examiner

*Primary Examiner* — Sean E Conley
(74) *Attorney, Agent, or Firm* — Kirk Dorius; Reed & Scardino LLP

(57) ABSTRACT

An ultraviolet sanitizer for non-contact sanitizing of handheld devices includes a device receptacle moveable adjacent a UV light source within a housing. The receptacle and a housing closure are moveable in response to detection of receipt of a handheld device in the receptacle.

7 Claims, 8 Drawing Sheets

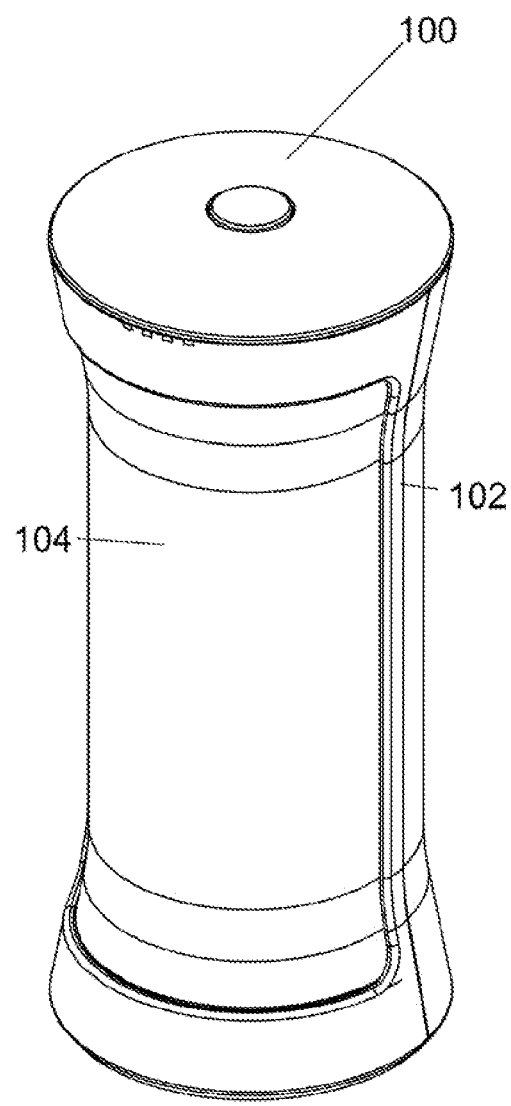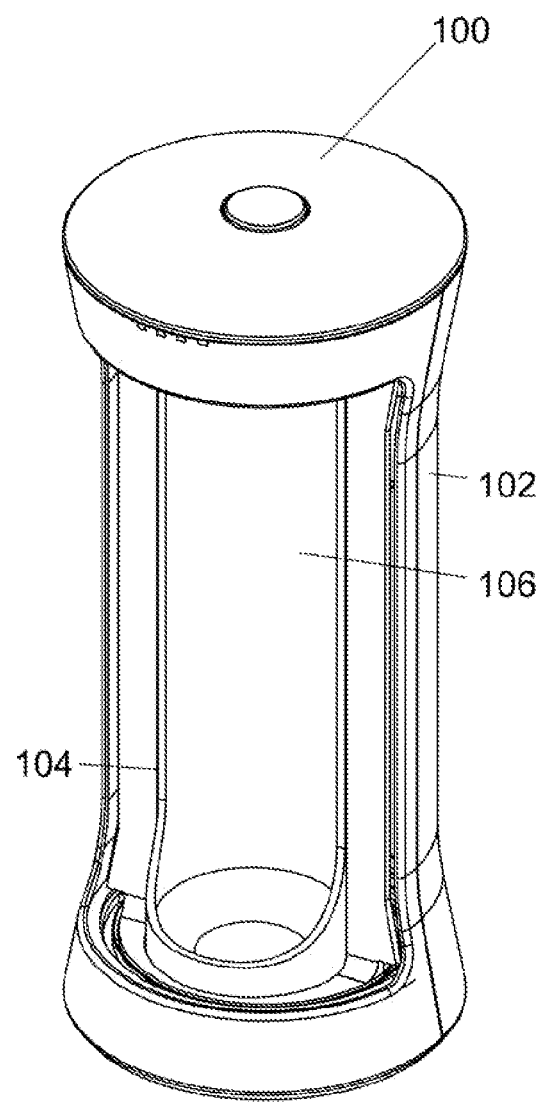
Fig. 1a                    Fig. 1b

| ITEM NO. | PART NUMBER | QTY. |
|---|---|---|
| 1 | CORE MOUNT | 1 |
| 2 | LIGHT CARRIER MOUNT | 1 |
| 3 | REMOTE CRADLE | 1 |
| 4 | SLEW RING GEAR | 1 |
| 5 | BASE MOLDING | 1 |
| 6 | FRONT COVER | 1 |
| 7 | SLIDE DOOR | 1 |
| 8 | BACK COVER | 1 |
| 9 | PCB ASSEMBLY | 1 |
| 10 | UV LIGHT BULB | 2 |
| 11 | MOTOR BRACKET | 1 |
| 12 | DRIVE MOTOR | 1 |
| 13 | TOP COVER | 1 |
| 14 | MAIN POWER BUTTON | 1 |
| 15 | BOTTOM COVER | 1 |

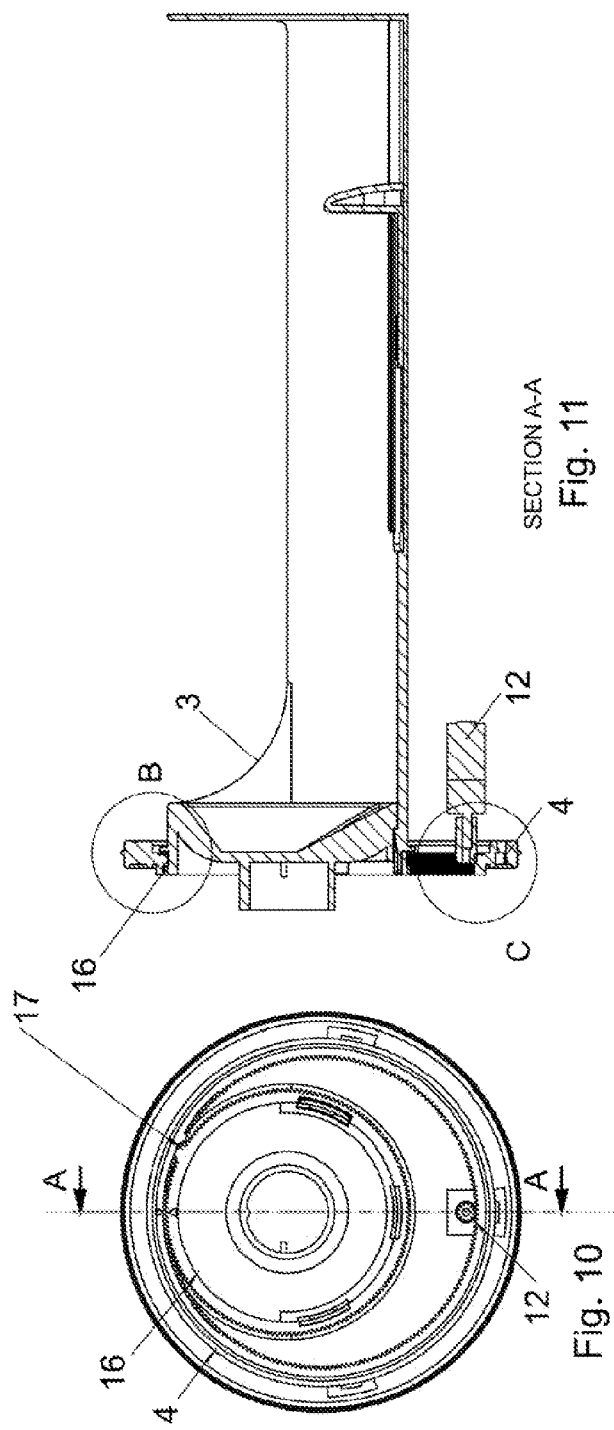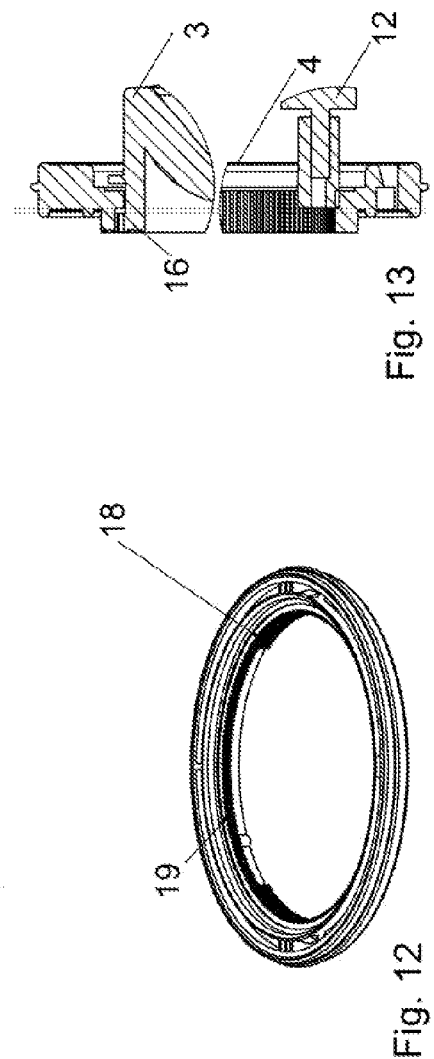

SANITIZING REMOTE CONTROLS AND HANDHELD DEVICES

CROSS-REFERENCE TO RELATED APPLICATION

This application claims priority to provisional application Ser. No. 61/832,794, filed Jun. 8, 2013, entitled Sanitizing Remote Controls and Handheld Devices, which is incorporated herein by reference in its entirety.

FIELD OF INVENTION

This invention generally relates to sanitation of handheld devices, and in particular, to sanitation by ultraviolet (UV) irradiation of such devices.

BACKGROUND OF THE INVENTION

Personal handheld devices such as smart phones and more communal handheld devices such as AV remotes can become vectors for spread of diseases as the surfaces become contaminated in handling. AV remotes in hotels and cruise ships present particular risks for spreading of diseases via surface contact. Accordingly, improvements are sought in sanitation of handheld devices, particularly in shared or communal handheld device applications.

SUMMARY OF THE INVENTION

While the way that the present invention addresses the disadvantages of the prior art will be discussed in greater detail below, in general, the present invention provides a reliable, efficient, non-contact means for sanitizing commonly shared handheld devices such as AV remotes, smart phones, computer input devices and the like. Many handheld devices include manual push buttons, mouth pieces, and various ports that can harbor problematic bacterial, fungal, and viral colonies, particularly in hotel rooms, cruise ship suites, common areas, and other high-turnover areas.

Wet wipes and antiseptic wipes are generally inadequate to reach all of the various facets and surfaces of the many buttons and ports common to such handheld devices. In contrast, the present invention directs UV light to each of the exposed facets and surfaces to effectively sanitize the device between handling by different users. Moreover, UV can effectively treat antibiotic resistant bacteria strains.

One aspect of the invention features, in various implementations, an apparatus for sanitizing handheld devices. The apparatus includes a housing defining a device insertion port and an ultraviolet (UV) light source disposed within the housing for irradiating handheld devices, e.g., A/V remote controls. The apparatus includes a receptacle, e.g., cradle or dock, within the housing for receiving a handheld device and a closure moveable to substantially cover the device insertion port. A first drive mechanism is operable to move the closure to substantially cover the device insertion port during the irradiating. The receptacle is movable by the same or a second drive mechanism to present different surfaces of the handheld device to the UV light source.

In some implementations, the receptacle is movable by at least one of the first drive mechanism and a second drive mechanism to position at least a portion of the receptacle between the UV light source and the device insertion port and closure.

In some implementations, the apparatus further includes a highly-reflective material present on an interior surface of the housing to redirect light to otherwise difficult to reach surfaces and facets. Reflection of the UV light within the chamber provides uniform irradiation of the various surfaces and facets of the handheld device.

In some implementations, the receptacle and the closure are rotatable relative to the housing to provide double barriers to escape of UV light from the housing at the device insertion port.

In some implementations, a sensor is configured to detect receipt of a handheld device within the receptacle. In some implementations, the sensor comprises a capacitance sensor positioned to detect the handheld device.

In some implementations, the cycle of receptacle movement and UV irradiation is initiated in response to detection of receipt of a handheld device.

In some implementations, the apparatus is further configured to reverse a direction of motion of at least one of the receptacle and the closure in response to detection of an impediment to such movement.

In some implementations, the apparatus includes a near-field charger positioned to charge a handheld device positioned in the receptacle.

In some implementations, the receptacle is moveable during at least a portion of the predetermined period to present different surfaces of a handheld device to the UV light source.

Another aspect of the invention features, in some applications, a method of sanitizing a handheld device. The method includes receiving a handheld device within a moveable receptacle disposed within a housing and detecting receipt of the handheld device in the receptacle. The method further includes initiating movement of at least one of the receptacle and a closure associated with the housing in response to detecting receipt of the handheld device and initiating an irradiation cycle by the UV light source in response to attainment of a predetermined position during movement of the at least one of the receptacle and the closure.

In some applications, the method includes presenting a reflective surface on an interior of at least one of the housing and the receptacle. The reflective surface can immerse the handheld device with the UV light while only a portion of the handheld device is positioned opposite the UV light source.

In some applications, the method includes moving the receptacle to position the handheld device substantially within a light cone of the UV light source.

In some applications, the method includes positioning at least a portion of the receptacle during the irradiation cycle between the closure and UV light source to provide a double barrier to escape of UV light from the housing.

In some applications, the method includes moving the receptacle during the irradiation cycle to present a range of surfaces of the handheld device to the UV light source.

In some applications, the method includes moving the receptacle to position the handheld device for retrieval from the housing upon completion of the irradiation cycle.

In some applications, the method includes positioning a near-field charger in proximity to the receptacle to charge the handheld device received in the receptacle.

In some applications, the method includes providing variable irradiation cycle times in response to identification of the handheld device.

In some applications, the method includes replacing an interchangeable receptacle within the housing to accommodate a second device.

In some applications, the method includes combining the housing with a display device, wherein the housing is configured to store a handheld remote control device for at least one of the display device and an audio/video input device in communication with the display device.

In some applications, the method includes providing a second visible spectrum light source to illuminate at least a portion of an exterior of at least one of the housing and the closure during the irradiation cycle to create an optically benign impression of the irradiation process underway within the housing.

BRIEF DESCRIPTION OF THE DRAWINGS

A more complete understanding of present invention may be derived by referring to the detailed description and claims when considered in connection with the Figures.

FIG. 1a illustrates an exemplary handheld device sanitizer according to one embodiment having a housing and a moveable closure.

FIG. 1b illustrates the handheld device sanitizer of FIG. 1a with the moveable closure retracted to allow access to handheld device receptacle within a housing of the sanitizer.

FIG. 10 is a bottom view of the drive mechanism and gear train of the sanitizer of FIGS. 9a-b.

FIG. 11 is a cross-sectional view of the sanitizer of FIGS. 9a-10, taken along the line A-A of FIG. 10.

FIG. 12 is a perspective view of the slew ring showing the different heights of gear tracks.

FIG. 13 shows detail breakouts of FIG. 11 juxtaposed to illustrate engagement track alignment.

DETAILED DESCRIPTION

Figure 2:
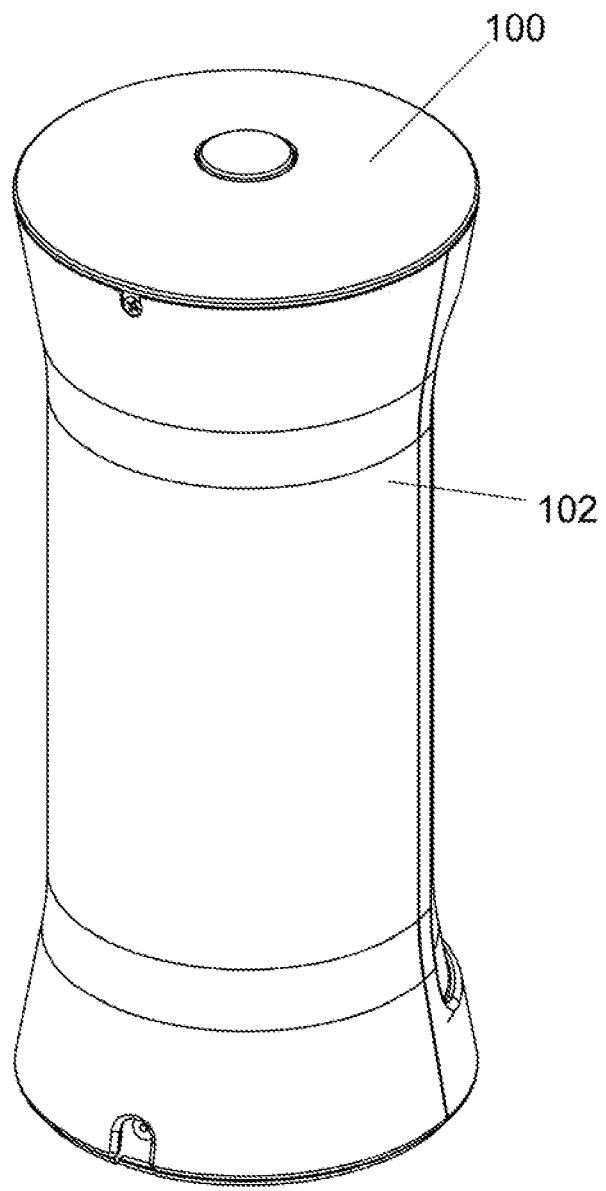
FIG. 2 is a rear view of the sanitizer of FIG. 1.
Figure 3A:
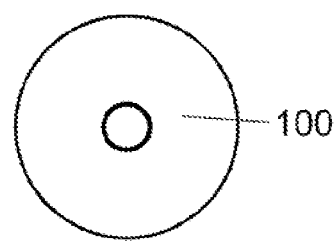
FIGS. 3a-e illustrate respective top, left side, front, right side, and bottom views of the sanitizer of FIG. 1.
Figures 3B, 3C, 3D:
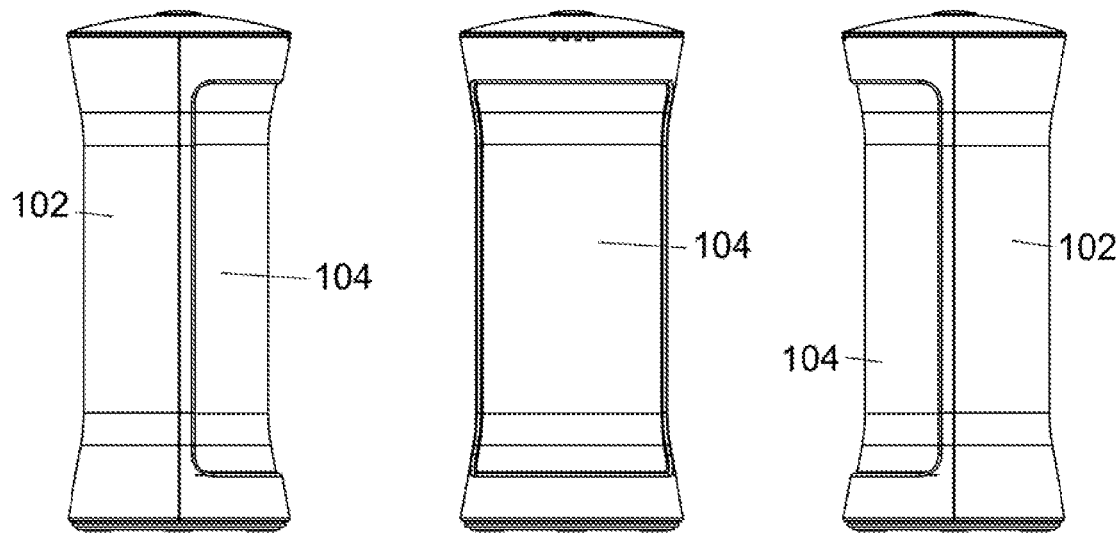
Figure 3E:
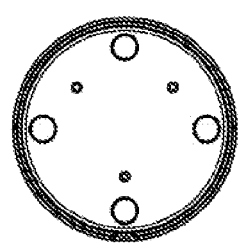
Figure 4:
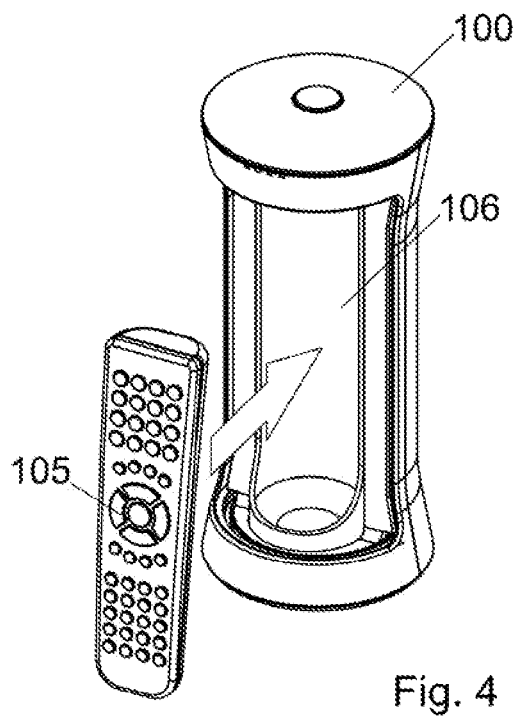
FIGS. 4-5 illustrate front perspective views of a sanitizer embodiment having a receptacle configured to receive an A/V remote.
Figure 5:
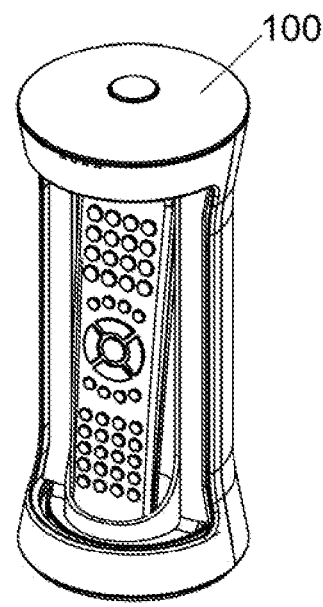
Figure 6:
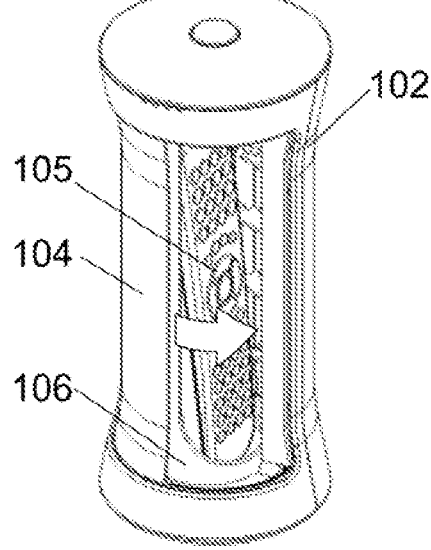
FIG. 6 illustrates the sanitizer of FIGS. 4-5 wherein the receptacle and a closure are rotatable in preparation for an irradiation cycle.
Figure 7:
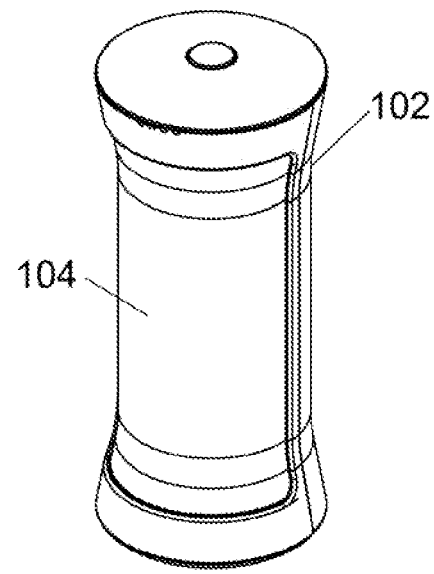
FIG. 7 illustrates the sanitizer of FIGS. 4-6 wherein the closure is rotated into a substantially UV-sealed positioned during irradiation.

The following description is of exemplary embodiments of the invention only and is not intended to limit the scope, applicability or configuration the invention. Rather, the following description is intended to provide a convenient illustration for implementing various embodiments of the invention. As will become apparent, various changes may be made in the function and arrangement of the elements described in these embodiments without departing from the scope of the invention as set forth herein. It should be appreciated that the description herein may be adapted to be employed with alternatively configured devices having different shapes, components, drive mechanisms, light sources and the like and still fall within the scope of the present invention. Thus, the detailed description herein is presented for purposes of illustration only and not of limitation.

Reference in the specification to "one embodiment" or "an embodiment" is intended to indicate that a particular feature, structure, or characteristic described in connection with the embodiment is included in at least an embodiment, implementation or application of the invention. The appearances of the phrase "in one embodiment" or "an embodiment" in various places in the specification are not necessarily all referring to the same embodiment.

With reference to the implementation illustrated in FIGS. 1-9, a UV sanitizer 100 for handheld devices includes a housing 102 with a receptacle 106 for receiving the handheld devices. Receptacle 106 and a housing closure 104 are moveable, e.g., rotatable, to substantially seal housing 102 against escape of UV light emitted from a UV light source within housing 102 during operation.

A sensor associated with the receptacle 106 detects receipt of a handheld device 105 and a controller initiates a sanitation cycle in response to the detection of handheld device 105. For example, a capacitance sensor, RFID antennae, through beam sensor, contact switch or other suitable sensor, can generate an input to the controller to indicate receipt or presence of handheld device 105 in receptacle 106. Receptacle 106 positions handheld device 105 for direct irradiation and/or incident, e.g., reflected, irradiation from the UV light source. Closure 104 is configured to substantially seal housing 102 against escape of UV light and to mitigate user exposure. In some implementations, the receptacle body, e.g., a sidewall, is positionable between the UV light source and closure 104 to provide a further barrier exposure of users to the UV light.

Following a period of irradiation, closure 104 and/or receptacle 106 are positioned to allow access for retrieval of handheld device 105. In some implementations, receptacle 106 may further serve as a dock to store and/or charge handheld device 105.

Figure 8:
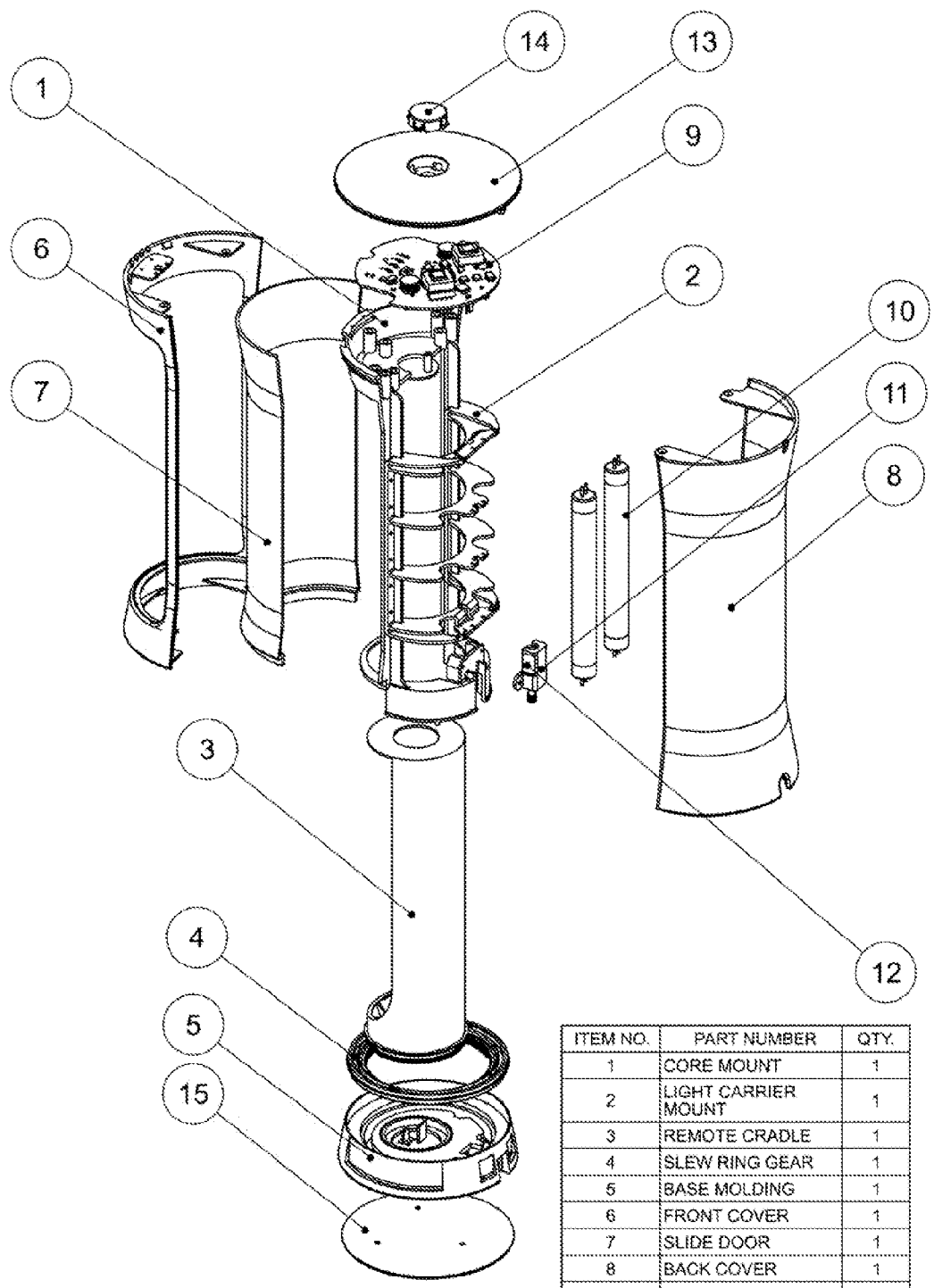
FIG. 8 is an exploded view of the sanitizer embodiment of FIGS. 4-7.

With reference to FIG. 8, housing 102 includes a front cover 6, back cover 8, and a sliding/rotating door or closure 7. Closure 7 is rotatable between a closed position adjacent front cover 6 and an open position adjacent back cover 8. A receptacle 3, e.g., remote cradle, is movable atop a base 5 via a drive mechanism 12. A PCB assembly 9 includes one or more controllers for providing power to a UV light source 10 and to drive mechanism 12. Examples of suitable UV light sources are mercury vapor UV lights emitting between about 185 nm and 254 nm UV light.

A slew ring gear 4 is interposed between receptacle 3 and base 5 in rotational engagement with drive mechanism 12. An indexing feature or catch between receptacle 2 and closure 7 causes closure 7 to follow rotation of receptacle 2 via a common drive mechanism. The indexing feature can allow for a rotational offset between movement of receptacle 2 and closure 7. This rotational offset can be configured to allow a brief period of viewing of receptacle movement before closure movement. A hard stop or position of either of the receptacle or closure can be used to initiate power to the UV light source. Of course, in some embodiments, closure 7 can be moveable independent of receptacle 2 and vice versus.

In some embodiments, the interior of the housing includes a highly reflective coating or polished surface to reflect the UV light to provide incident as well as direct irradiation to an increased number of handheld device surfaces. In some implementations, UV light sources may be provided at multiple locations around the receptacle.

The various system components can be constructed from any number of suitable materials, including polymers, metals or composite materials, e.g., via forming, extrusion, injection molding, compression molding, machining etc. The sanitation system may be free standing or installed in any convenient location, e.g., freestanding on table or nightstand, or attached to a wall or display device. Alternatively, the sanitizer system may be integrated with a display device, e.g., with a display frame or stand, or integrated with any other device associated with a handheld accessory device such as an AV remote control. The sanitizer may thus serve as a dock or a charger for the handheld device.

The sanitizer system can include a hard on/off power switch, e.g., located on the top (illustrated), back, front or side, and the power switch may be illuminated at power on. Power may be provided from a wall outlet, USB port, powered accessory port, or an on-board battery.

With continued reference to FIG. 8, during rotation of receptacle 3 and closure 7, the drive mechanism including drive motor 12 engages the main ring gear 4, e.g., in a rack and pinion configuration. Drive motor 12 is mounted to an inner rim of stationary base 5 of the sanitizer device. Cradle or receptacle 3 includes a small gear ring (not shown) on its lower end that interfaces with main gear ring 4 on the opposite side of the inside diameter from the motor mounting. The gear teeth are oriented such that the interface of the motor spur gear to main gear ring 4 is on the inside diameter of main ring gear 4. Motor 12 includes a reduction gearbox to reduce the revolutions to approximately 120-150 rpm. In the illustrated embodiment, closure door 7 is mounted to main ring gear 4 and rotates with it.

Figures 9A, 9B:
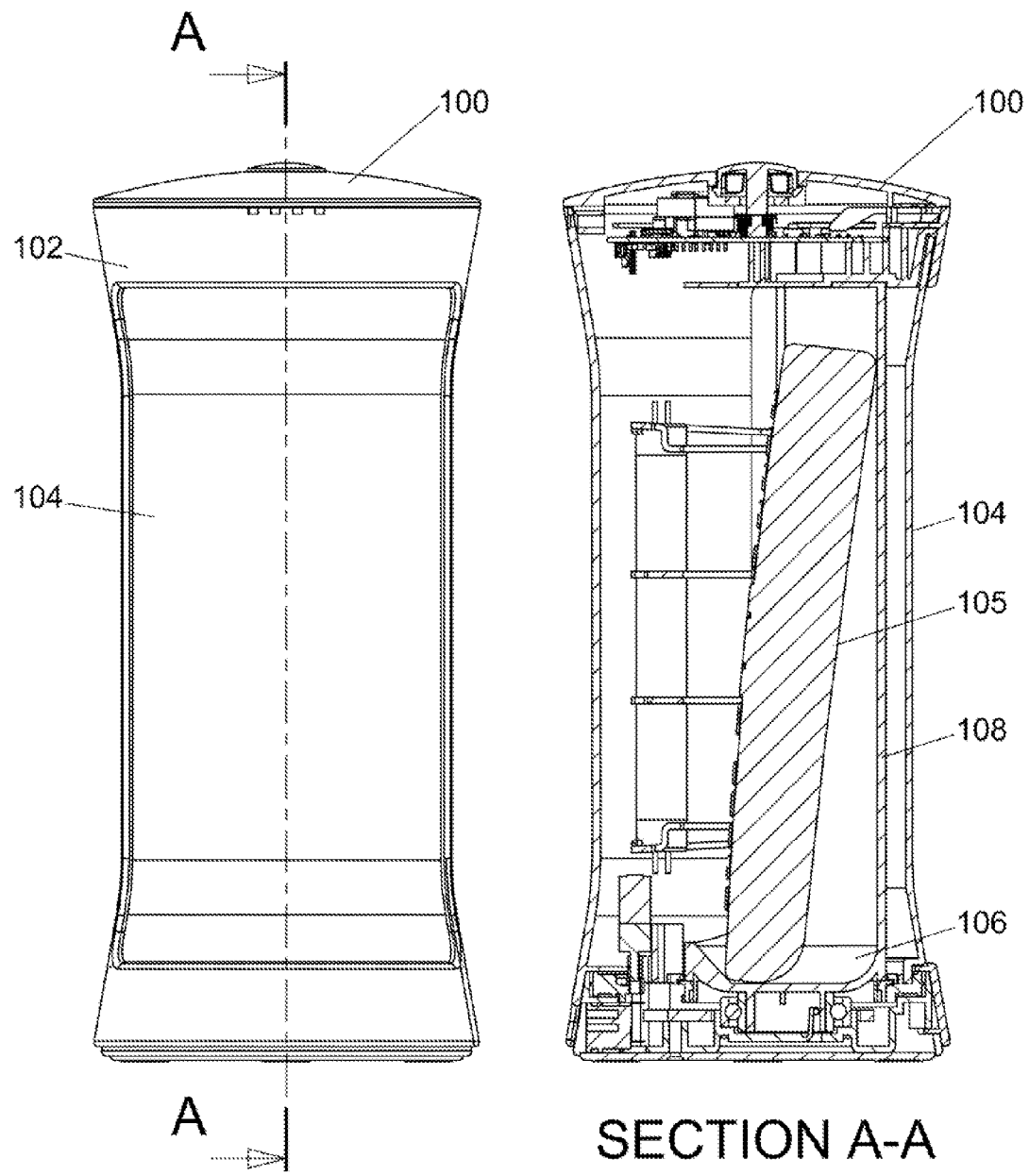
FIG. 9a is a front view of the assembled sanitizer of FIG. 8.
FIG. 9b is a schematic cross-section through sanitizer along line A-A of FIG. 9a, showing the position of the remote control relative to the light during the irradiation cycle.

With reference to FIG. 9b a schematic cross-section through sanitizer 100 along line A-A of FIG. 9a, illustrates positioning of handheld device 105 adjacent the UV light source during an irradiation cycle. The receptacle sidewall 108 and closure 104 provide a double barrier to emissions from the UV light to protect the user.

With reference to FIG. 10, a bottom view of the drive mechanism and gear train illustrates slew ring gear or main ring gear 4 driven by drive motor 12 and engaging spindle gear 16 at the bottom of receptacle 3. Locking bump 17 serves to stop rotation of spindle gear 16, e.g., when the receptacle 3 and closure door 7 are in the open position. Cradle or receptacle 3 rotates around its own axis on a low-friction bearing and rotates as the main ring gear 4 rotates. Thus, motor 12 drives main ring gear 4 which in turn drives the smaller spindle gear 16 of cradle/receptacle 3.

Activation of motor 12 drives main gear ring 4, which rotates about 15 degrees before engaging smaller spindle gear 16, which then also begins to rotate. Once main ring gear 4 has rotated about 180 degrees, closure door 7 reaches a hard stop molding in the plastic. This causes a surge in the current drawn by motor 12 and the controller disengages the power to the motor. The delayed rotation of smaller spindle gear 16 positions remote 105 with the keypad facing UV lights 10.

A timer in the drive control software informs the system when door 7 has rotated beyond a point where a human hand could be the cause of a hard stop. If a hard stop is detected before the timer runs out, it is assumed that the stop was caused by a foreign object e.g., user hand, or jam and drive motor 12 retracts door 7 and reinitializes to fully open. To reinitialize, the door is automatically rotated backward to an "open hard stop" upon power up.

With reference to FIG. 11, a cross-sectional view taken along A-A of FIG. 10 illustrates receptacle 7 and associated drive train including spindle gear 16, which is driven by main ring gear 4, which is driven in turn by drive motor 12. Details B and C are enlarged in FIG. 12.

With reference to FIG. 12, slew ring or main ring 4 is illustrated with two different heights of gear tracks, a full-height track portion 18 and a half-height track portion 19. Due to the difference in diameters of spindle gear 16 and main ring gear 4, the dual-track system allows main ring 4 to rotate closure door 7 fully while avoiding over-rotation of the spindle gear 16. The gear teeth on the cradle spindle gear 16 are similarly reduced to slightly less than half the height of main ring gear 4 as and section 19 of ring gear 4 is reduced to the same dimension, so that when the reduced-height section 19 of main ring gear 4 rotates past the contact point with cradle spindle gear 16, it does no longer engages the smaller spindle gear 16.

With reference to FIG. 13, Details B and C of FIG. 11 are juxtaposed to illustrate engagement track alignment and clearance.

Figure 14:
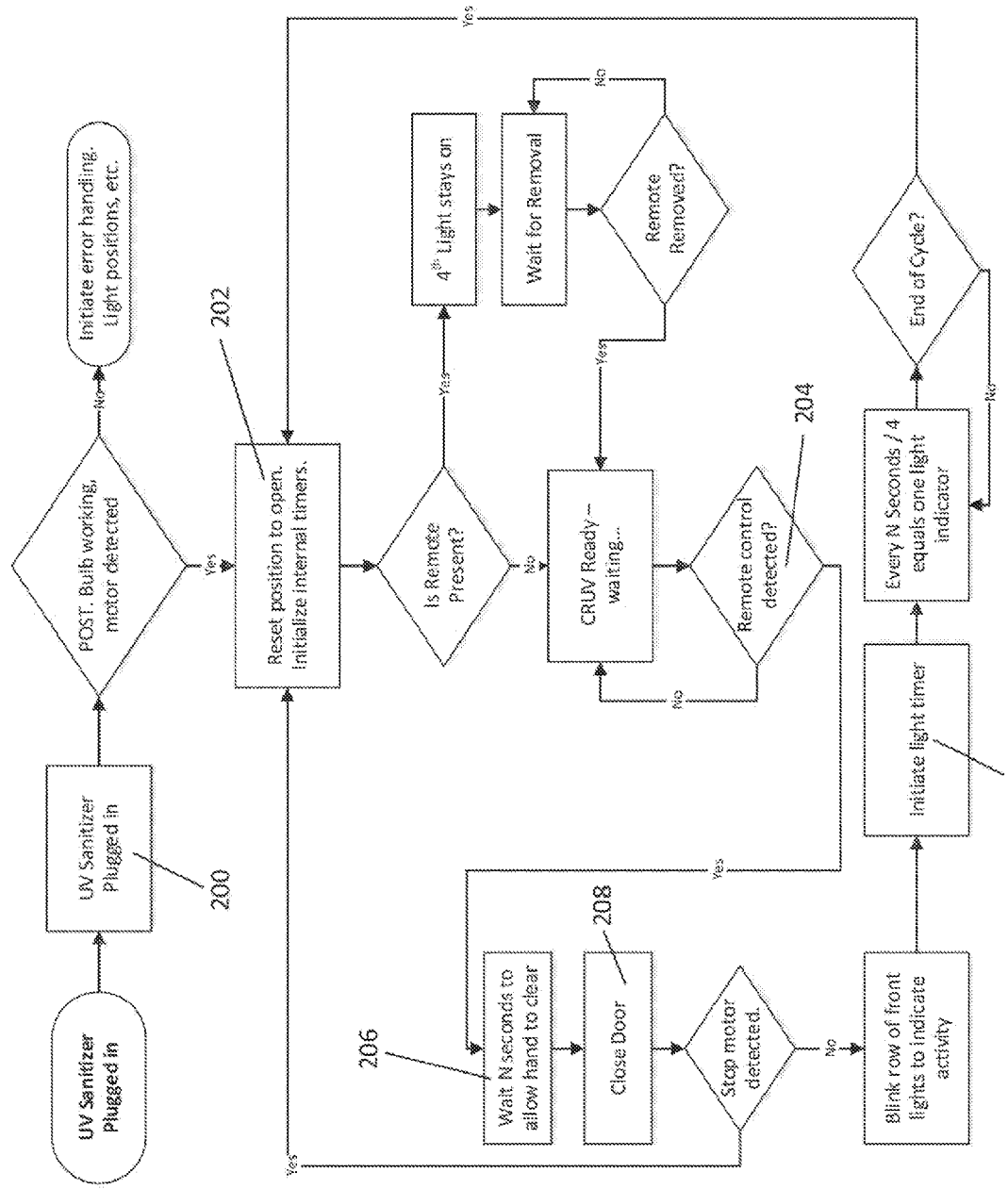
FIG. 14 is a flow chart of one application of a method of touchless UV sanitation.

With reference to FIG. 14, a method of touchless sanitation is described according to one application of aspects of the present invention. The sanitizes is initialized upon connection to a power source. (200) Initialization can include system diagnostics such as verifying operability of bulbs and drive mechanisms or resetting system defaults such as receptacle or closure positioning, cycle timers and the like. (202) Once initialized, a sanitizer control module continually monitors for input(s) from one or more sensors configured to detect receipt in the receptacle of a handheld device to be sanitized. (204) Device sensing can be accomplished using any number or combination of through beams, contact switches, RFID antennae, capacitance sensors, or other suitable physical, optical or electrical detection means or sensors.

In response to the input from the one or more sensors, the sanitizer initiates a sanitation cycle. The controller allows a predetermined period for clearance of a user's hand or instruments after detection of the handheld device. (206) The controller then causes a drive mechanism to move a closure "door" across an opening in the housing, e.g., to substantially seal the housing against escape of UV light generated within the housing. (208) The drive mechanism can also move the receptacle, e.g., via rotation, to better position the remote for direct irradiation by the UV light source. In some applications, a common drive mechanism can motivate both the closure and the receptacle into a predetermined position for irradiation of the handheld device. Desired positioning of the closure and/or receptacle can be obtained, e.g. by monitoring one or more of the amperage drawn on the drive mechanism, a period of drive mechanism operation, inputs received from limit switches or other position or range of travel sensors. Presence of an obstacle such as a user's fingers or dislodged remote may be detected by similar means such that the controller can cease or reverse movement of the closure and/or receptacle.

The controller further causes as power supply to provide electrical power to a UV light source within the housing for a predetermined period of time. (210) The cycle time can be varied as a function of detection of a particular type of handheld device or by user selection. Variable cycle times can thus accommodate a wider range of devices and varying standards for sanitation for different applications, e.g., home use versus hospital use. Indicators such as external LEDs and/or audible signals can be provided to indicate any number of phases of system readiness or operation. For example, different colors or numbers of illuminated LEDs can indicate a power state, system readiness, an irradiation activity, and a completed cycle state. Upon completion of an irradiation cycle, the controller causes the drive mechanism to return the closure and/or receptacle to a starting position or to another position to provide access for removal of the sanitized handheld device. (202) The controller can then reinitialize the system to a ready state for a subsequent cycle.

To monitor the presence of the device to be cleaned as well as the presence of a person's hand as they deposit or remove the controller receives input from a capacitive sensor. One suitable controller is a Cypress PSoC® MCU with integrated CapSense® building blocks which receives input from a monopole wire antenna. Using the CapSense® capability of the MCU, the self-capacitance of the antenna can be established as a baseline. Infrared detection can also be used to detect the presence of a user's hand or of the device.

The presence of the handheld device to be cleaned causes an increased level of capacitance which is detected by the antenna. The presence of a human hand either removing or replacing the device further increases the capacitance detected by the antenna. Using the detected capacitance levels established above, the control system recognizes when the device to be cleaned is placed in the cradle, and when the hand is removed, leaving only the device in the cradle. The control system initiates an irradiation cycle in response to these inputs. When the hand is removed, the control system waits a set period of time and then causes the motor to close the closure door. If a hand or other obstacle causes unexpected resistance to movement of the closure door or receptacle, the control system stops the movement, retracts the closure door, and reinitiates the system.

Accordingly, the present invention provides a nearly touchless system and method for sanitation of handheld devices. Various alternative embodiments may include interchangeable or multiple cradles for varied or multiple handheld devices. Similarly, the receptacle can be configured to accommodate a particular device or a range of devices, including medical or personal hygiene devices.

Similarly, while the present invention has been described herein as a sanitizer system, the present invention may be readily combined with any number of existing devices now known or hereafter developed. For example, the sanitizer system could be designed to include a night light, clock, radio, or alarm clock. Similarly, any number of system surfaces could be configured to receive product or consumer branding or other advertising, labels or instructions.

Finally, while the present invention has been described above with reference to various exemplary embodiments, many changes, combinations and modifications may be made to the exemplary embodiments without departing from the scope of the present invention. For example, the various components may be implemented in alternative ways. These alternatives can be suitably selected depending upon the particular application or in consideration of any number of factors associated with the operation of the device. In addition, the techniques described herein may be extended or modified for use with other types of devices. These and other changes or modifications are intended to be included within the scope of the present invention.

What is claimed is:

1. An apparatus for sanitizing handheld devices comprising:
    a housing defining a device insertion port;
    an ultraviolet (UV) light source disposed within the housing for irradiating handheld devices;
    a receptacle disposed within the housing to receive a handheld device therein;
    a sensor configured to detect receipt of the handheld device within the receptacle;
    a closure moveable to substantially cover the device insertion port;
    a first drive mechanism operable to move the closure to substantially cover the device insertion port during the irradiating;
    wherein the receptacle is movable during the irradiating to present different surfaces of the handheld device to the UV light source; and
    wherein the apparatus is configured such that detection by the sensor of receipt of the handheld device in the receptacle initiates movement of the closure, initiates movement of the receptacle, and initiates the irradiating.

2. The apparatus of claim 1, further comprising a reflective material present on an interior surface of the housing.

3. The apparatus of claim 1, wherein the receptacle and the closure are rotatable relative to the housing to provide double barriers to escape of light from the UV light source at the device insertion port.

4. The apparatus of claim 1, where the sensor comprises a capacitance sensor.

5. The apparatus of claim 1, further configured to reverse a direction of motion of at least one of the receptacle and the closure in response to detection of an impediment to such motion.

6. The apparatus of claim 1, further comprising a near-field charger positioned to charge the handheld device positioned in the receptacle.

7. The apparatus of claim 1, wherein the receptacle is moveable by at least one of the first drive mechanism and a second drive mechanism to position a portion of the receptacle between the UV light source and the insertion port or closure.

* * * * *